United States Patent
Ooshima et al.

(10) Patent No.: US 9,402,589 B2
(45) Date of Patent: Aug. 2, 2016

(54) X-RAY CT APPARATUS AND METHOD FOR CONTROLLING THE SAME

(71) Applicant: Toshiba Medical Systems Corporation, Otawara-shi (JP)

(72) Inventors: Noriyuki Ooshima, Utsunomiya (JP); Takahito Watanabe, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 412 days.

(21) Appl. No.: 13/859,041

(22) Filed: Apr. 9, 2013

(65) Prior Publication Data

US 2013/0266117 A1    Oct. 10, 2013

(30) Foreign Application Priority Data

Apr. 9, 2012 (JP) ................ 2012-088401

(51) Int. Cl.
| | |
|---|---|
| *A61B 6/03* | (2006.01) |
| *A61B 6/04* | (2006.01) |
| *A61B 6/02* | (2006.01) |
| *A61B 6/00* | (2006.01) |

(52) U.S. Cl.
CPC ............ *A61B 6/0407* (2013.01); *A61B 6/027* (2013.01); *A61B 6/032* (2013.01); *A61B 6/0457* (2013.01); *A61B 6/54* (2013.01)

(58) Field of Classification Search
CPC .... A61B 6/032; A61B 6/0407; A61B 6/4233; A61B 6/027; A61B 6/0457; A61B 6/54; A61B 6/547
See application file for complete search history.

(56) References Cited

U.S. PATENT DOCUMENTS

| | | | |
|---|---|---|---|
| 2005/0094761 A1* | 5/2005 | Hagiwara | ............ 378/15 |
| 2006/0140339 A1* | 6/2006 | Marcovitch | ............ 378/20 |

FOREIGN PATENT DOCUMENTS

| | | |
|---|---|---|
| CN | 101419178 A | 4/2009 |
| JP | 1995-313501 | 12/1995 |

(Continued)

OTHER PUBLICATIONS

Combined Chinese Office Action and Search Report issued Oct. 17, 2014 in Patent Application No. 201310120597.9 (with Japanese language translation and English translation of categories of cited documents).

(Continued)

*Primary Examiner* — Glen Kao
*Assistant Examiner* — Chih-Cheng Kao
(74) *Attorney, Agent, or Firm* — Oblon, McClelland, Maier & Neustadt, L.L.P.

(57) ABSTRACT

An X-ray CT apparatus according to an embodiment includes: an X-ray irradiator configured to emit X-rays to the examinee on a table; an X-ray detector configured to detect X-rays transmitted through the examinee on the table; a data collector configured to collect transmission data on those X-rays; a movement drive unit configured to move one of the table and the X-ray irradiator relative to the other in an outward direction and then in a homeward direction, the outward direction and homeward direction being opposite directions along a body axis of the examinee on the table; a position detector configured to detect a relative position between the table and the X-ray irradiator; and a data collection controller configured to control timings for starting and stopping data collection by the data collector, based on the relative position between the table and the X-ray irradiator.

4 Claims, 4 Drawing Sheets

(56) References Cited

FOREIGN PATENT DOCUMENTS

| | | |
|---|---|---|
| JP | 2006-320523 | 11/2006 |
| JP | 2007-312878 | 12/2007 |
| JP | 2009-101086 A | 5/2009 |
| JP | 2010-268827 | 12/2010 |
| JP | 2010-269042 A | 12/2010 |
| JP | 2011-62445 | 3/2011 |

OTHER PUBLICATIONS

Japanese Office Action mailed Dec. 15, 2015 in Japanese Patent Application No. 2012-088401.

* cited by examiner

X-RAY CT APPARATUS AND METHOD FOR CONTROLLING THE SAME

CROSS-REFERENCE TO THE RELATED APPLICATION

This application is based on and claims the benefit of priority from Japanese Patent Applications No. 2012-88401, filed on Apr. 9, 2012; the entire contents of which are incorporated herein by reference.

FIELD

Embodiments described herein relate generally to an X-ray CT apparatus and a method for controlling the X-ray CT apparatus.

BACKGROUND

An X-ray CT apparatus (X-ray computed tomography imaging apparatus) irradiates an examinee, such as a patient, with X-rays and detects X-rays transmitted through the examinee. A data collecting device of the X-ray CT apparatus then collects X-ray transmission data which is based on the amount of X-rays detected. Thereafter, the X-ray CT apparatus performs reconstruction processing on the X-ray transmission data, and generates a slice image (a tomographic image) of the examinee.

An example of such an X-ray CT apparatus which has been developed is configured to image an examinee using an X-ray irradiator and an X-ray detector located opposite each other with the examinee on a table in between, while rotating them about the body axis of the examinee. This X-ray CT apparatus performs imaging by shuttle helical scan. In the shuttle helical scan, the examinee is imaged while a table on which the examinee lies down is moved with its moving direction being changed alternately between two directions along the body axis of the examinee i.e., a direction from the feet to the head and a direction from the head to the feet.

In this shuttle helical scan, a certain target region of the examinee on the table is imaged by collecting X-ray transmission data based on a time period determined by the number of views (a time period converted from the number of views) with the moving speed of the table being constant (within an allowable speed range). Note that the number of views is obtained from the number of rotations of the X-ray irradiator and the X-ray detector about the body axis of the examinee.

In the shuttle helical scan, the shuttling movement of the table tends to make the movement of the table inconstant. Thus, the distance travelled by the table within a certain time period (i.e., the moving speed of the table) tends to vary. Further, the rotational speed of the X-ray irradiator and the X-ray detector might also vary to change the width covered by one view. Thus, when imaging is controlled based on the number of views (a time period), an imaging target region, namely a data collection region for collecting X-ray transmission data, is not always fixed.

For example, a timing for ending data collection is usually controlled based on the number of views after the start of the collection. Hence, in a case of imaging only a certain site which is a part of an examinee (a certain imaging target region), if the timing for ending the data collection is early, the data collection region becomes narrow, so that a necessary amount of X-ray transmission data cannot be obtained. Reversely, if the timing for ending the data collection is late, the data collection region becomes wide, so that the X-ray transmission data are collected more than necessary. In this way, the data collection region for collecting the X-ray transmission data is not always fixed, which makes it difficult to accurately image an imaging target region.

DETAILED DESCRIPTION

According to one embodiment, an X-ray CT apparatus comprises: a table on which an examinee lies down; an X-ray irradiator configured to emit X-rays to the examinee on the table; an X-ray detector configured to detect X-rays transmitted through the examinee on the table; a data collector configured to collect transmission data on the X-rays detected by the X-ray detector; a movement drive unit configured to move one of the table and the X-ray irradiator relative to another one of the table and the X-ray irradiator in an outward direction and then in a homeward direction, the outward direction being one of directions along a body axis of the examinee on the table, and the homeward direction being another one of the directions along the body axis; a position detector configured to detect a relative position between the table and the X-ray irradiator; and a data collection controller configured to control timings for starting and stopping the data collection by the data collector, based on the relative position between the table and the X-ray irradiator detected by the position detector.

According to another embodiment, provided is a method for controlling an X-ray CT apparatus including a table on which an examinee lies down, an X-ray irradiator configured to emit X-rays to the examinee on the table, an X-ray detector configured to detect X-rays transmitted through the examinee on the table, a data collector configured to collect transmission data on the X-rays detected by the X-ray detector, and a movement drive unit configured to move one of the table and the X-ray irradiator relative to another one of the table and the X-ray irradiator in an outward direction and then in a homeward direction, the outward direction being one of directions along a body axis of the examinee on the table, and the homeward direction being another one of the directions along the body axis. The method comprises the steps of: detecting, by a position detector, a relative position between the table and the X-ray irradiator; and controlling, by a data collection controller, timings for starting and stopping the data collection by the data collector, based on the detected relative position between the table and the X-ray irradiator.

An embodiment is described with reference to the drawings.

Figure 1:
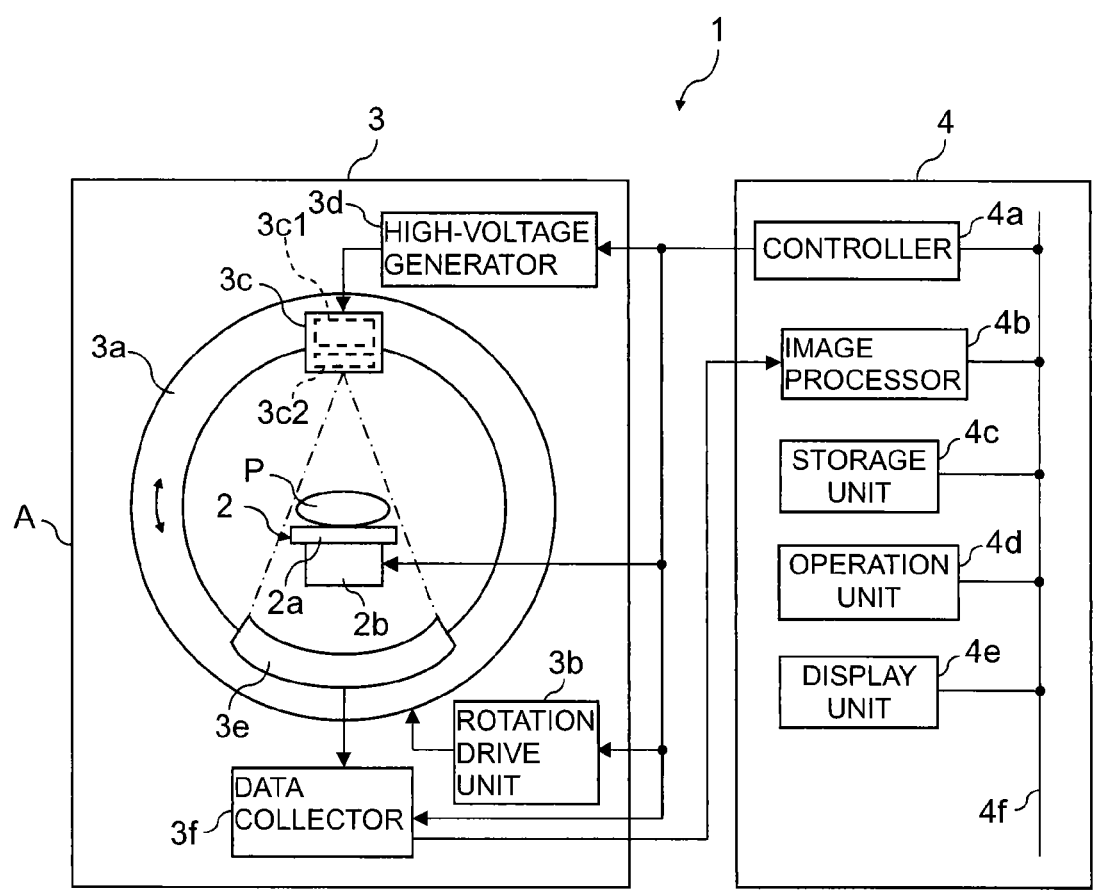
FIG. 1 is a diagram schematically showing the configuration of an X-ray CT apparatus according to an embodiment.

As shown in FIG. 1, an X-ray CT apparatus (X-ray computed tomography imaging apparatus) 1 according to this embodiment includes a bed 2 on which an examinee P, such as a patient, lies down, an imaging device 3 configured to image the examinee P on the bed 2, and a control device 4 configured to control the bed 2 and the imaging device 3.

The bed 2 includes a rectangular table 2a on which the examinee P is placed and a movement drive unit 2b configured to support the table 2a and move the table 2a in horizontal directions and vertical directions (up and down directions). The movement drive unit 2b has a movement mechanism for moving the table 2a, a drive source for supplying a driving power for moving the table 2a, and the like. The movement drive unit 2b of the bed 2 moves the table 2a up to a desired height and then moves the table 2a horizontally to transfer the examinee P on the table 2a to a desired position.

The imaging device 3 includes a rotator 3a provided rotatably inside a gantry A, which is a chassis, a rotation drive unit 3b configured to rotate the rotator 3a, an X-ray irradiator 3c configured to emit X-rays, a high-voltage generator 3d configured to supply the X-ray irradiator 3c with a high voltage, an X-ray detector 3e configured to detect X-rays transmitted through the examinee P on the table 2a, and a data collector 3f configured to collect the X-rays detected by the X-ray detector 3e as X-ray transmission data (X-ray amount distribution data).

The rotator 3a is a ring-shaped rotational frame configured to support components such as the X-ray irradiator 3c and the X-ray detector 3e and rotate. The rotator 3a is held by the gantry A rotatably. The X-ray irradiator 3c and the X-ray detector 3e are located on the rotator 3a at positions opposite each other so that the examinee P on the table 2a may be located in between them, and they rotate around the examinee P about the body axis of the examinee P.

The rotation drive unit 3b is located inside the gantry A of the imaging device 3. The rotation drive unit 3b drives the rotator 3a to rotate as controlled by the control device 4. For example, the rotation drive unit 3b rotates the rotator 3a in one direction at a predetermined rotation speed based on a control signal sent from the control device 4.

The X-ray irradiator 3c is fixed to the rotator 3a and includes an X-ray tube 3c1 configured to emit X-rays and an X-ray diaphragm 3c2, such as a collimator, configured to narrow the X-rays emitted by the X-ray tube 3c1. Specifically, the X-ray irradiator 3c is configured such that X-rays emitted by the X-ray tube 3c1 are narrowed by the X-ray diaphragm 3c2 so that the examinee P on the table 2a may be irradiated with a beam of X-rays having a fan beam shape with a cone angle, e.g., a pyramid shape.

Note that various types of an X-ray diaphragm can be used as the X-ray diaphragm 3c2. An example of an X-ray diaphragm usable here is one configured to move two X-ray stopping plates made of lead or the like in directions away from and toward each other to appropriately change the size of the opening (gap) formed by the X-ray stopping plates.

The high-voltage generator 3d is located inside the gantry A of the imaging device 3. The high-voltage generator 3d is a device for generating a high voltage to be supplied to the X-ray tube 3c1 of the X-ray irradiator 3c, and is configured to step-up or rectify a voltage given by the control device 4 and supply the stepped-up or rectified voltage to the X-ray tube 3c1. To cause the X-ray tube 3c1 to generate X-rays as desired, the control device 4 controls the waveform of a voltage to give to the high-voltage generator 3d, i.e., various conditions such as the amplitude and pulse width.

The X-ray detector 3e is fixed to the rotator 3a at a position opposite the X-ray irradiator 3c. The X-ray detector 3e converts X-rays transmitted through the examinee P on the table 2a into electric signals and sends them to the data collector 3f. As the X-ray detector 3e, a multilayered, multichannel X-ray detector can be used. The multilayered, multichannel X-ray detector is configured with X-ray detection elements configured to detect X-rays and arranged in lattice. Specifically, a channel is formed by multiple (e.g., several hundreds to several thousands of) X-ray detection elements arranged in a channel direction (i.e., a direction about the body axis of the examinee P), and multiple (e.g., 16 or 64) rows of such a channel are arranged in a slice direction (i.e., in a direction of the body axis of the examinee P).

The data collector 3f is located inside the gantry A of the imaging device 3, and configured to collect the electrical signals sent from the X-ray detector 3c as X-ray transmission data (X-ray amount distribution data), and send this X-ray transmission data to the control device 4.

The control device 4 includes a controller 4a configured to control each unit, an image processor 4b configured to perform various kinds of image processing on the X-ray transmission data, a storage unit 4c configured to store various programs, various kinds of data, and the like, an operation unit 4d configured to receive an operation inputted by the user, and a display unit 4e configured to display images. The controller 4a, the image processor 4b, the storage unit 4c, the operation unit 4d, and the display unit 4e are electrically connected to each other via a bus line 4f.

Based on the various programs and data stored in the storage unit 4c, the controller 4a controls units such as the movement drive unit 2b of the bed 2 and the rotation drive unit 3b and the high-voltage generator 3d of the imaging device 3. In addition, the controller 4a controls the diaphragm 3c2 of the X-ray irradiator 3c, and also controls display of various images, such as slice images (tomographic images) and scanograms (positioning images), on the display unit 4e. For example, a central processing unit (CPU) or the like can be used as the controller 4a.

The image processor 4b performs various types of image processing, such as preprocessing for obtaining projection data from the X-ray transmission data sent from the data collector 3f, image reconstruction processing for performing image reconstruction on the projection data, and scanogram generation processing for generating scanograms. For example, an array processor or the like can be used as this image processor 4b.

The storage unit 4c is a storage device configured to store various programs, various kinds of data, and the like. Examples of the various kinds of data include slice images and scanograms. For example, a read-only memory (ROM), a random access memory (RAM), a hard disk (magnetic disk device), a flash memory (semiconductor disk device), or the like can be used as the storage unit 4c.

The operation unit 4d is an input unit configured to receive various operations inputted on the input unit 4d by a user, such as instructing imaging, displaying an image, switching between images, and making various settings. For example, input devices such as a keyboard, a mouse, and a control lever can be used as the operation unit 4d.

The display unit 4e is a display device configured to display various types of images, such as an X-ray image and a scanogram of the examinee P and an operation screen. For example, a liquid crystal display, a CRT-based display, or the like can be used as the display unit 4e.

The X-ray CT apparatus 1 has various imaging modes, including for example a scanogram mode for acquiring scanograms and a tomography mode for acquiring slice images. Examples of the tomography mode include a regular multi-slice scan mode (normal CT), a helical scan mode (helical CT), a variable helical pitch scan mode, and a shuttle helical scan mode.

In the scanogram mode, scanograms for positioning or setting an imaging range (scan range) are acquired prior to the imaging in the tomography mode. For example, in scan planning, scanograms are acquired in advance, and the scanograms are displayed on the display 4e. A user checks the scanograms, and operates the operation unit 4d to set an imaging range.

A scanogram is acquired as follows. First, the X-ray irradiator 3c and the X-ray detector are fixed at a predetermined position, i.e., a predetermined view angle (e.g., 0° or 90°). Then, while the table 2a of the bed 2 is moved in the direction of the body axis of the examinee P to a predetermined position, X-ray transmission data are collected by causing the X-ray irradiator 3c to irradiate the examinee P on the table 2a with X-rays, and the X-ray detector 3e to detect X-rays transmitted through the examinee P on the table 2a. Thereafter, the collected X-ray transmission data are processed by the image processor 4b to generate a scanogram, which is then saved in the storage unit 4c and also displayed on the display unit 4e.

In the helical scan mode, a slice image is acquired while the table 2a is moved at a constant speed (within an allowable speed range) in one direction along the body axis of the examinee P (e.g., in a direction from the feet to the head). There are also a variable helical scan mode in which the speed of the table 2a is changed during the imaging according to an imaging target site or the like and a shuttle helical scan mode in which a slice image is acquired while the moving direction of the table 2a is changed alternately between two directions along the body axis of the examinee P (e.g., a direction from the feet to the head and a direction from the head to the feet). In this way, the X-ray CT apparatus 1 is capable of X-ray imaging in various imaging modes.

A slice image is acquired as follows. First, X-ray transmission data are collected (an imaging target region is scanned) by causing the X-ray irradiator 3c to irradiate the examinee P on the table 2a with X-rays and the X-ray detector to detect X-rays transmitted through the examinee P on the table 2a, while the rotation drive unit 3b rotates the X-ray irradiator 3c and the X-ray detector 3e about the body axis of the examinee P on the table 2a, and also while the movement drive unit 2b moves the table 2a in the direction of the body axis of the examinee P. Thereafter, the collected X-ray transmission data are processed by the image processor 4b to generate a slice image, which is then saved in the storage unit 4c and also displayed on the display unit 4e.

In the shuttle scan, such a scan is repeated by shuttling the table 2a so that the imaging target region of the examinee P on the table 2a is imaged a number of times. Specifically, the moving direction of the table 2a is changed alternately between two directions along the body axis of the examinee P (e.g., a direction from the feet to the head and a direction from the head to the feet) to image the imaging target region of the examinee P on the table 2a a predetermined number of times (e.g., several tens of times).

Next, the controller 4a mentioned above is described in detail with reference to FIG. 2.

Figure 2:
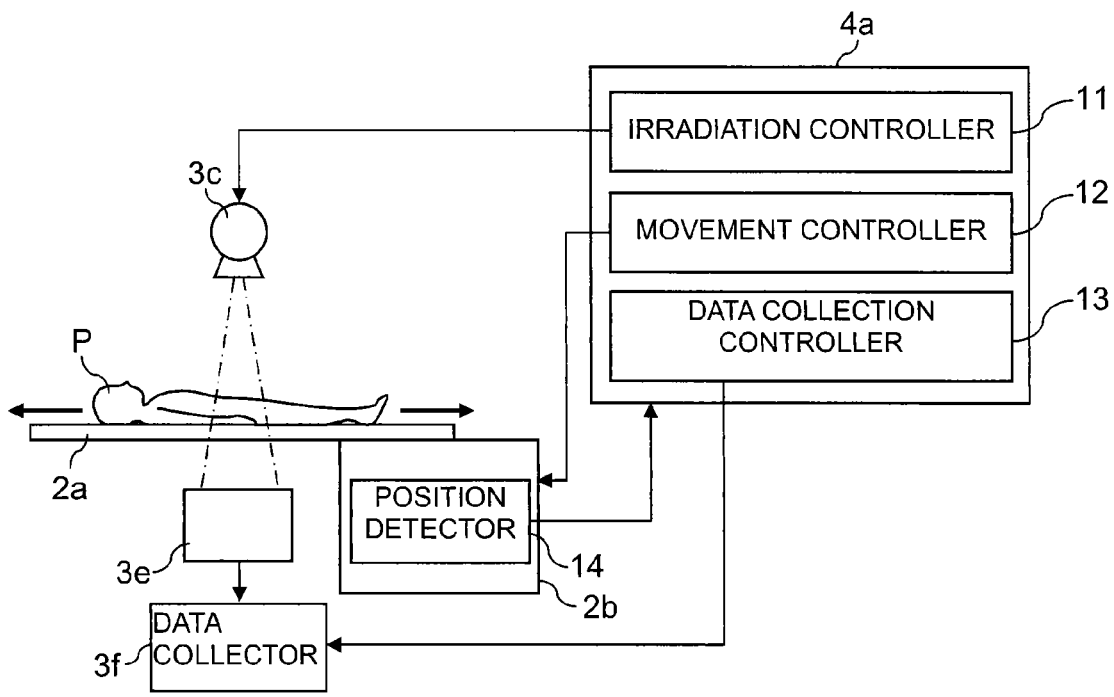
FIG. 2 is a diagram schematically showing the configuration of a controller, along with a bed and (part of) an imaging device of the X-ray CT apparatus according to the embodiment.

As shown in FIG. 2, the controller 4a has an irradiation controller 11 configured to control the irradiation by the X-ray irradiator 3c, a movement controller 12 configured to control the movement drive unit 2b of the bed 2, and a data collection controller 13 configured to control the data collection by the data collector 3f.

Note that the movement drive unit 2b has a position detector 14 configured to detect the position of the table 2a, which is a mobile object, and to output information on the detected position of the table 2a to the controller 4a. For example, an encoder can be used as the position detector 14. The encoder is attached to, for example, a drive source, such as a motor, of the movement drive unit 2b.

Based on the information on the position of the table 2a detected by the position detector 14, the irradiation controller 11 instructs the X-ray irradiator 3c to start or stop irradiation. Specifically, the irradiation controller 11 gives this instruction by outputting an irradiation start signal or an irradiation stop signal to the X-ray irradiator 3c, which then starts or stops X-ray irradiation accordingly.

Based on the information on the position of the table 2a detected by the position detector 14, the movement controller 12 instructs the movement drive unit 2b to start or stop moving the table 2a. Specifically, the movement controller 12 gives this instruction by outputting a movement start signal or a movement stop signal to the movement drive unit 2b, which then starts or stops moving the table 2a accordingly.

Based on the information on the position of the table 2a detected by the position detector 14, the data collection controller 13 gives the data collector 3f instructions related to data collection, such as starting or stopping collection of X-ray transmission data. Specifically, the data collection controller 13 gives this instruction by outputting a data collection start signal or a data collection stop signal to the data collector 3f, which then starts or stops collection of X-ray transmission data accordingly.

Note that the irradiation controller 11, the movement controller 12, and the data collection controller 13 may be configured by hardware such as electric circuits, or may be configured by software such as programs executing their functions, or may be configured by a combination of both.

Figure 3:
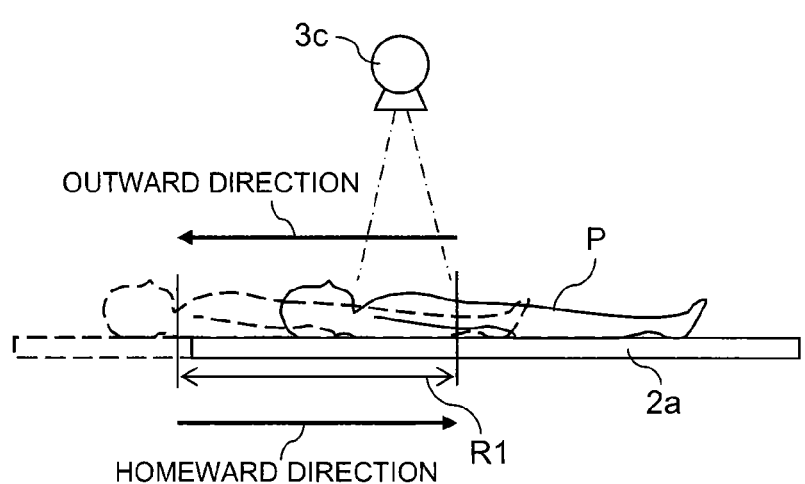
FIG. 3 is a diagram illustrating the shuttling movement of a table in shuttle helical scan according to the embodiment.
Figure 4:
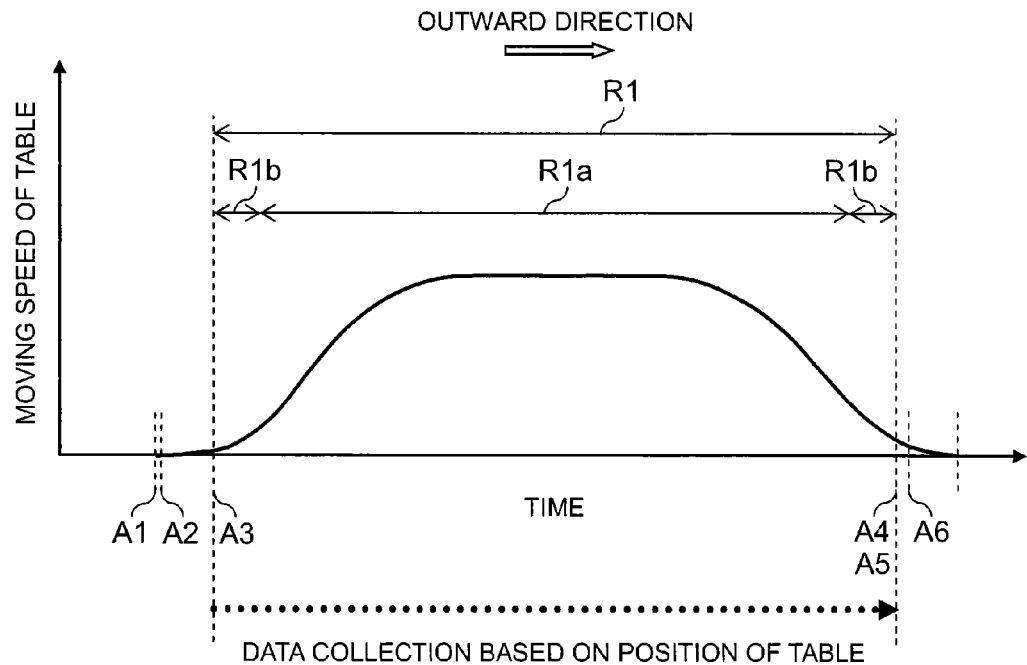
FIG. 4 is a graph showing a temporal change in the speed of the table moving in an outward direction in shuttle helical scan according to the embodiment.
Figure 5:
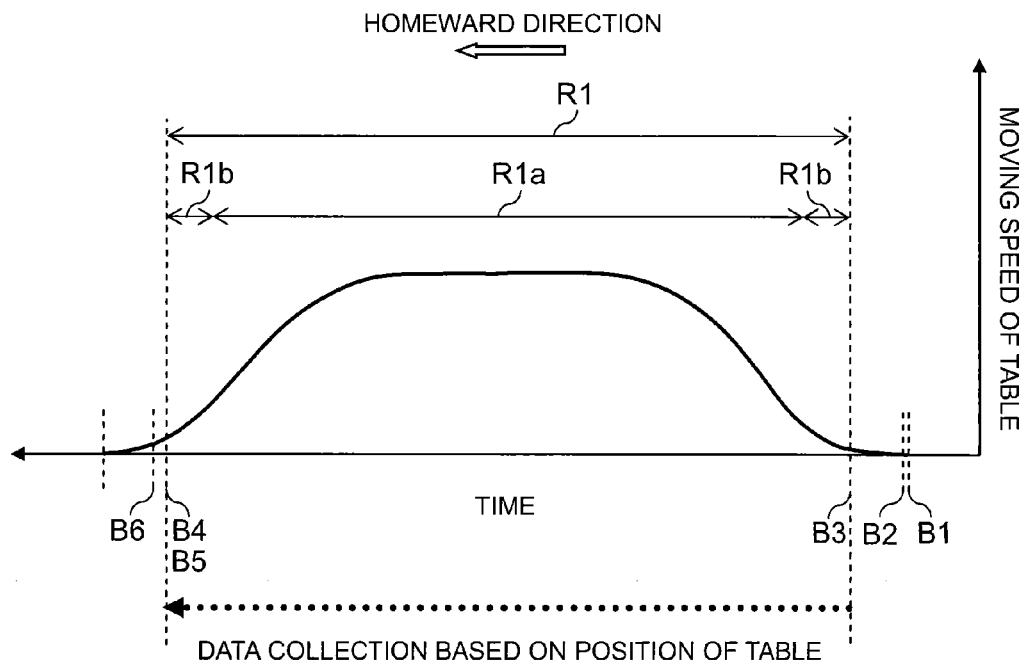
FIG. 5 is a graph showing a temporal change in the speed of the table moving in a homeward direction in shuttle helical scan according to the embodiment.

With reference to FIGS. 3 to 5, a description is given of imaging performed when the imaging mode is the shuttle helical scan mode.

As shown in FIG. 3, in the shuttle helical scan mode, the table 2a repeats its shuttling movement along the body axis of the examinee P on the table 2a a predetermined number of times (e.g., several tens of times), the shuttling movement including an outward movement from the feet to the head (an outward direction) and then a homeward movement from the head to the feet (a homeward direction). Thereby, the table 2a and the X-ray irradiator 3c move relative to each other in the outward direction and the homeward direction to image only an imaging target region R1. Note that the number of shuttling movements can be set at will when necessary.

As shown in FIG. 4, in the outward movement, the moving speed of the table 2a changes with time. Specifically, the moving speed of the table 2a gradually increases up to a certain maximum speed value (a predetermined set value), and then gradually decreases after a lapse of a predetermined time period since the moving speed reached the maximum speed value.

In the outward movement, first, based on the positional information on the table 2a, the irradiation controller 11 outputs an irradiation start signal A1 to the X-ray irradiator 3c, and then the movement controller 12 outputs a movement start signal A2 for the table 2a to the movement drive unit 2b. Thereby, the X-ray irradiator 3c starts its irradiation, and the movement drive unit 2b starts moving the table 2a. Note that the timings for outputting the irradiation start signal A1 and the movement start signal A2 may be reversed.

Thereafter, when the table 2a reaches an imaging start position (a data collection start position), the data collection controller 13 outputs a data collection start signal A3 to the data collector 3f, which thereby starts collecting X-ray transmission data. Note that the data collection start signal A3 is outputted based on the positional information on the table 2a, and the data collector 3f starts collecting X-ray transmission data in response to the data collection start signal A3. The data collector 3f performs its data collection based on not time, but the positional information on the table 2a.

Next, when the table 2a reaches an imaging stop position (a data collection stop position), the irradiation controller 11 outputs an irradiation stop signal A4 to the X-ray irradiator 3c, and also the data collection controller outputs a data collection stop signal A5 to the data collector 3f. Collection of the X-ray transmission data is thus ended. Note that the irradiation stop signal A4 and the data collection stop signal A5 are outputted based on the positional information on the table 2a. The X-ray irradiator 3c stops irradiation in response to the irradiation stop signal A4, and the data collector 3f stops collection of the X-ray transmission data in response to the data collection stop signal A5.

Note that in the data collection described above, the irradiation stop signal A4 and the data collection stop signal A5 are outputted upon, for example, detection of a movement for the length of the imaging target region R1 (mm) from the collection start position at which data collection starts, which is set to 0 mm. For the imaging target region R1, a predetermined range R1b is added before and after an imaging range R1a set by the user. Thus, the imaging target region R1 is set as R1=R1a+R1b+R1b. The predetermined range R1b is a range for collecting data necessary for image reconstruction (a margin for variable helical pitch). The imaging range R1a is preset through an input operation made by the user with the operation unit 4d.

Thereafter, the movement controller 12 outputs a movement stop signal A6 for the table 2a to the movement drive unit 2b based on the positional information on the table 2a. The movement drive unit 2b thus stops driving the table 2a, and the table 2a completely stops after moving by inertia. Lastly, the movement controller 12 confirms the stop of the table 2a.

As shown in FIG. 5, the moving speed of the table 2a changes with time in the homeward movement, too. As in the case of the outward movement, the moving speed of the table 2a gradually increases up to a certain maximum speed value (a predetermined set value), and then gradually decreases after a lapse of a predetermined time period since the moving speed reached the maximum speed value.

In the homeward movement, first, based on the positional information on the table 2a, the irradiation controller 11 outputs an irradiation start signal B1 to the X-ray irradiator 3c, and then, the movement controller 12 outputs a movement start signal B2 for the table 2a to the movement drive unit 2b. Thereby, the X-ray irradiator 3c starts its irradiation, and the movement drive unit 2b starts moving the table 2a. Note that the timings for outputting the irradiation start signal A1 and the movement start signal A2 may be reversed.

Thereafter, when the table 2a reaches an imaging start position (a data collection start position), the data collection controller 13 outputs a data collection start signal B3 to the data collector 3f, which thereby starts collecting X-ray transmission data. Note that the data collection start signal B3 is outputted based on the positional information on the table 2a, and the data collector 3f starts collecting X-ray transmission data in response to the data collection start signal B3. The data collector 3f performs its data collection based on not time, but the positional information on the table 2a.

Next, when the table 2a reaches an imaging stop position (a data collection stop position), the irradiation controller 11 outputs an irradiation stop signal B4 to the X-ray irradiator 3c, and also the data collection controller outputs a data collection stop signal B5 to the data collector 3f. Collection of the X-ray transmission data is thus ended. Note that the irradiation stop signal B4 and the data collection stop signal B5 are outputted based on the positional information on the table 2a. The X-ray irradiator 3c stops irradiation in response to the irradiation stop signal B4, and the data collector 3f stops collection of the X-ray transmission data in response to the data collection stop signal B5.

Note that in the data collection described above, as in the case of the outward movement, the irradiation stop signal B4 and the data collection stop signal B5 are outputted upon, for example, detection of a movement for the length of the imaging target region R1 (mm) from the collection start position at which data collection starts, which is set to 0 mm. For this reason, even when the movement of the table 2a is inconstant or when the rotation of the rotator 3a is inconstant, the imaging target region R1 is fixed, having the same size as that imaged in the outward movement.

Further, since the data collection is performed based on the positional information on the table 2a, the position covered by one view is always fixed.

Thereafter, the movement controller 12 outputs a movement stop signal B6 for the table 2a to the movement drive unit 2b based on the positional information on the table 2a. The movement drive unit 2b thus stops driving the table 2a, and the table 2a completely stops after moving by inertia. Lastly, the movement controller 12 confirms the stop of the table 2a.

The shuttle helical scan is completed by repeating such a shuttling operation a predetermined number of times through the above-described control. If the end of data collection is controlled based on the number of views (a time period) completed after the start of the collection, the following can happen. Specifically, if the timing for ending the data collection (i.e., timings for ending irradiation and data collection: see A4 and A5 in FIG. 4 and B4 and B5 in FIG. 5) is early, the data collection region (the imaging target region R1) becomes narrow, so that a necessary amount of X-ray transmission data cannot be obtained. Reversely, if the timing for ending the data collection is late, the data collection region becomes wide, so that the X-ray transmission data are collected more than necessary. Thus, if the timing for ending the data collection is controlled based on the number of views (a time period), the data collection region for collecting the X-ray transmission data is not always fixed.

To overcome such a problem, data collection is controlled according to the positional information on the table 2a, or more specifically, the data collector 3f is instructed to start and stop collection of X-ray transmission data based on the positional information on the table 2a. As a result, the data collection region can be fixed without being influenced by the inconstant movement of the table 2a and the inconstant rotation of the rotator 3a. Thus, by controlling the data collection based on the positional information on the table 2a, the data collection region, namely, the imaging target region R1 can always be fixed.

Since the data collection is performed based on the positional information on the table 2a, data can be collected for the same position for both of the outward and homeward movements without being influenced by the inconstant movement of the table 2a and the inconstant rotation of the rotator 3a. Thus, accurate images can be obtained.

Moreover, in the shuttle helical scan mode for observing a temporal change in the image data obtained by repeated data collection for the same region, data collected by one outward movement and its homeward movement within the same view are always results of imaging the same bed position; therefore, image comparison can be done accurately.

Figure 6:
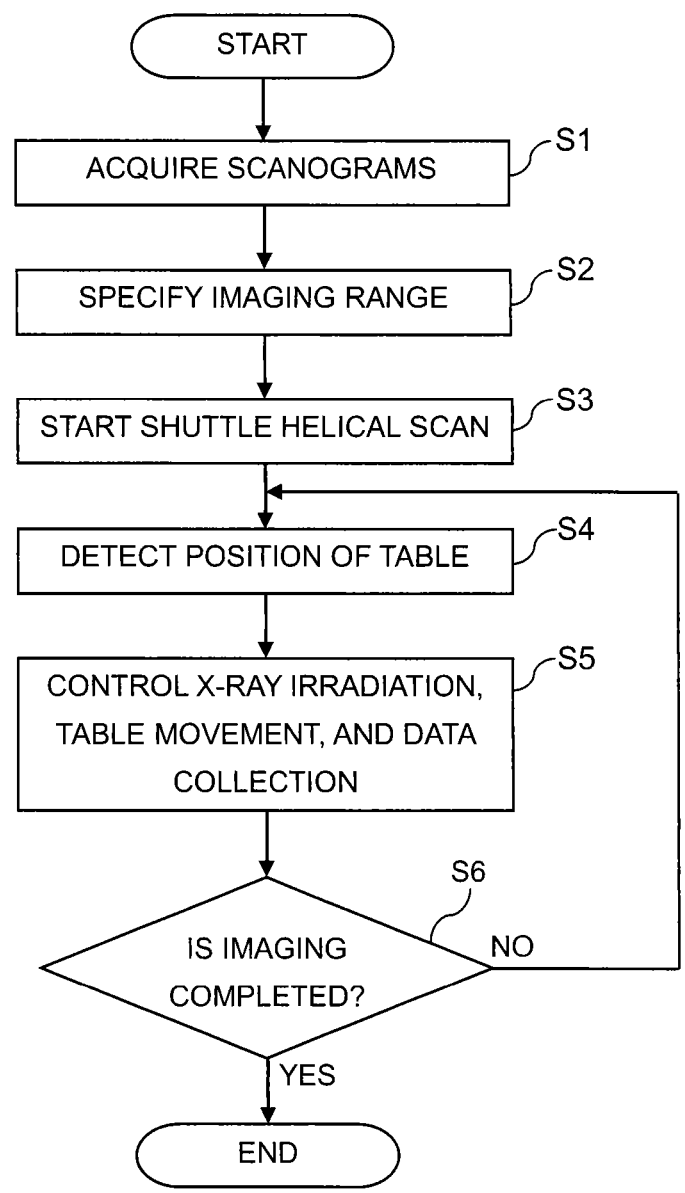
FIG. 6 is a flowchart showing a flow of imaging processing performed by the X-ray CT apparatus according to the embodiment.

Next, with reference to FIG. 6, a description is given of imaging processing performed by the X-ray CT apparatus 1 described above. Note that the shuttle helical scan mode is set as the imaging mode here.

As shown in FIG. 6, first, scanograms are acquired (Step S1), and the imaging range R1a of the examinee P is specified on the scanograms through an input operation made by a user with the operation unit 4d (Step S2). In this event, the scanograms are displayed on the display unit 4e, and the user specifies the imaging range R1a through an input operation with the operation unit 4d while visually checking the scanograms. The predetermined range R1b is added before and after the imaging range R1a thus specified; accordingly, the imaging target region R1 is set as R1=R1a+R1b+R1b.

Note that, in Step S1, the scanograms are acquired at positions of, for example, view angles 0° (plan position) and 90° (side position), respectively, and are stored in the storage unit 4c. At this time, the radiation field is set to maximum. At the 0° plan position, X-rays are applied to the upper face of the examinee P on the table 2a, and X-rays transmitted through the examinee P are detected. Thus, a scanogram in an AP direction (a front-rear direction) is acquired as a plan image of the examinee P. At the 90° side position, X-rays are applied to the side of the examinee P on the table 2a, and X-rays transmitted through the examinee P are detected. Thus, a scanogram in an LR direction (a left-right direction) is acquired as a side image of the examinee P.

After Step S2, shuttle helical scan is started for the imaging target region R1 thus set (Step S3). In the shuttle helical scan, as already described, slice images are acquired while the table 2a is moved with its moving direction being changed alternately between two directions along the body axis of the examinee P (e.g., a direction from the feet to the head and a direction from the head to the feet).

Once the shuttle helical scan is started in Step S3, the position detector 14 detects the position of the table 2a in accordance with the movement of the table 2a (Step S4), and X-ray irradiation, table movement, and data collection are controlled based on the positional information on the table 2a thus detected (Step S5).

In Step S5, as described above (see FIGS. 4 and 5), based on the positional information on the table 2a, the irradiation controller 11 gives the X-ray irradiator 3c instructions for, for example, starting or stopping the irradiation. Further, based on the positional information on the table 2a, the movement controller 12 gives the movement drive unit 2b instructions for, for example, starting or stopping to move the table 2a. Moreover, based on the positional information on the table 2a, the data collection controller 13 gives the data collector 3f instructions for, for example, starting or stopping to collect X-ray transmission data.

After Step S5, a judgment is made as to whether the imaging is completed or not (Step S6). If it is judged that the imaging is not completed (NO in Step S6), the processing returns to Step S4 to repeat the processing therefrom. If it is judged that the imaging is completed (YES in Step S6), the processing ends.

The judgment in Step S6 as to whether the imaging is completed or not is made by determining whether or not the table 2a has reached, and is stopped at, a predetermined imaging completion position. More specifically, since the imaging mode is the shuttle helical scan mode, a determination is made as to whether or not the table 2a has reached, and is stopped at, a predetermined imaging completion position after repeating the shuttling movement a predetermined number of times. Then, when it is determined that the table 2a has reached, and is stopped at, the predetermined imaging completion position, a judgment is made that the imaging is completed.

According to such imaging processing, the position of the table 2a is detected, and data collection is controlled based on that positional information. Since the data collection is thus controlled according to the positional information on the table 2a, a data collection region for collecting the X-ray transmission data, namely the imaging target region R1, can always be fixed without being influenced by the inconstant movement of the table 2a and the inconstant rotation of the rotator 3a. Since the shuttle helical scan involves shuttling movement of the table 2a, mechanical variations tend to occur. Nonetheless, by controlling data collection based on the positional information on the table 2a, such variations can be compensated for.

As described, according to the embodiment, the position of the table 2a is detected, and the data collector 3f is controlled as to its starting and stopping data collection based on the positional information thus detected. Thus, the data collection can be controlled according to the positional information on the table 2a; consequently, a data collection region for collecting the X-ray transmission data, namely the imaging target region R1, can always be fixed without being influenced by the inconstant movement of the table 2a and the inconstant rotation of the rotator 3a, i.e., mechanical variations. As a result, accurate imaging can be accomplished in the shuttle helical scan because the imaging target region R1 is always fixed.

In particular, the timings for starting and stopping data collection are controlled so that a data collection region of the examinee P on the table 2a for collecting the X-ray transmission data in the outward direction and that in the homeward direction can coincide with each other. Hence, the data collection region for collecting the X-ray transmission data, namely the imaging target region R1 can be reliably fixed, which allows accurate, more reliable imaging of the imaging target region R1 in the shuttle helical scan.

Moreover, data collection is controlled based on the positional information on the table 2a also during the data collection between the start and the end of the data collection. In other words, for example, data collection is controlled so that the position on the examinee P on the table 2a for collecting the X-ray transmission data in the outward direction and that in the homeward direction can coincide with each other. This allows data collection in the outward direction and data collection in the homeward direction to be performed for the same position without being influenced by the inconstant movement of the table 2a and the inconstant rotation of the rotator 3a. Hence, images obtained are accurate.

Although the position of the table 2a moving during imaging is detected in the above embodiment, the present invention is not limited to this as long as the relative position between the table 2a and the X-ray irradiator 3c can be detected and used. For example, if the X-ray CT apparatus 1 is of a type in which not the table 2a but the gantry A is moved by a movement drive unit (including, for example, a rail mechanism, a drive source, a position detector, and the like) during imaging, the gantry A including the X-ray irradiator 3c, the X-ray detector 3e, the rotator 3a, and the like is a mobile object. Hence, the position of the gantry A is detected and used.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
a table on which an examinee lies down;
an X-ray irradiator configured to emit X-rays to the examinee on the table;
an X-ray detector configured to detect X-rays transmitted through the examinee on the table;
a data collector configured to collect transmission data on the X-rays detected by the X-ray detector;
a movement drive unit configured to move one of the table and the X-ray irradiator relative to another one of the table and the X-ray irradiator in an outward direction and then in a homeward direction, the outward direction being one of directions along the body axis of the examinee on the table, and the homeward direction being another one of the directions along the body axis;
a position detector configured to detect a relative position between the table and the X-ray irradiator; and
a data collection controller configured to control start and stop of the data collection by the data collector, based on the relative position between the table and the X-ray irradiator detected by the position detector, wherein
the data collection controller controls the data collection by the data collector based on the relative position between the table and the X-ray irradiator detected by the position detector so that a position of the examinee on the table for collecting the transmission data is the same for the outward direction and for the homeward direction between the start of the data collection and the stop of the data collection, and
the data collection controller controls start and stop of the data collection by the data collector based on the relative position between the table and the X-ray irradiator detected by the position detector so that the start of the data collection is later than a movement start of the table and the stop of the data collection is earlier than a movement end of the table.

2. The X-ray CT apparatus according to claim 1, wherein the data collection controller controls start and stop of the data collection by the data collector based on the relative position between the table and the X-ray irradiator detected by the position detector so that a data collection region of the examinee on the table for collecting the transmission data is the same for the outward direction and for the homeward direction.

3. A method for controlling an X-ray CT apparatus including a table on which an examinee lies down, an X-ray irradiator configured to emit X-rays to the examinee on the table, an X-ray detector configured to detect X-rays transmitted through the examinee on the table, a data collector configured to collect transmission data on the X-rays detected by the X-ray detector, and a movement drive unit configured to move one of the table and the X-ray irradiator relative to another one of the table and the X-ray irradiator in an outward direction and then in a homeward direction, the outward direction being one of directions along a body axis of the examinee on the table, and the homeward direction being another one of the directions along the body axis, the method comprising the steps of:
detecting, by a position detector, a relative position between the table and the X-ray irradiator; and
controlling, by a data collection controller, timings for starting and stopping the data collection by the data collector, based on the detected relative position between the table and the X-ray irradiator, wherein
in the controlling step, the data collection by the data collector is controlled based on the detected relative position between the table and the X-ray irradiator so that a position of the examinee on the table for collecting the transmission data is the same for the outward direction and for the homeward direction between the start of the data collection and the stop of the data collection, and
in the controlling step, the timings for starting and stopping the data collection by the data collector are controlled based on the detected relative position between the table and the X-ray irradiator so that the start of the data collection is later than a movement start of the table and the stop of the data collection is earlier than a movement end of the table.

4. The method for controlling an X-ray CT apparatus according to claim 3, wherein
in the controlling step, the timings for starting and stopping the data collection by the data collector are controlled based on the detected relative position between the table and the X-ray irradiator so that a data collection region of the examinee on the table for collecting the transmission data is the same for the outward direction and for the homeward direction.

* * * * *